(12) United States Patent
Loewen

(10) Patent No.: US 9,408,736 B2
(45) Date of Patent: Aug. 9, 2016

(54) DEVICE FOR DEPLOYING AN IMPLANTABLE MEDICAL DEVICE

(71) Applicant: W. L. Gore & Associates, Inc., Newark, DE (US)

(72) Inventor: John L. Loewen, Salt Lake City, UT (US)

(73) Assignee: W. L. GORE & ASSOCIATES, INC., Newark, DE (US)

( * ) Notice: Subject to any disclaimer, the term of this patent is extended or adjusted under 35 U.S.C. 154(b) by 162 days.

(21) Appl. No.: 14/197,488

(22) Filed: Mar. 5, 2014

(65) Prior Publication Data

US 2014/0188209 A1 Jul. 3, 2014

Related U.S. Application Data

(63) Continuation of application No. 11/546,798, filed on Oct. 12, 2006, now Pat. No. 8,702,778.

(60) Provisional application No. 60/727,180, filed on Oct. 14, 2005.

(51) Int. Cl.
*A61F 2/06* (2013.01)
*A61F 2/966* (2013.01)
*A61F 2/95* (2013.01)

(52) U.S. Cl.
CPC . *A61F 2/966* (2013.01); *A61F 2/95* (2013.01); *A61F 2002/9517* (2013.01)

(58) Field of Classification Search
CPC .... A61F 2002/9517; A61F 2/95; A61F 2/966
USPC ................................................ 623/1.11, 1.12
See application file for complete search history.

(56) References Cited

U.S. PATENT DOCUMENTS

| | | |
|---|---|---|
| 4,386,621 A | 6/1983 | Redl |
| 5,707,376 A | 1/1998 | Kavteladze et al. |
| 5,788,707 A | 8/1998 | Del Toro et al. |
| 6,336,606 B1 | 1/2002 | Smithson et al. |
| 7,326,236 B2 | 2/2008 | Andreas et al. |
| 2004/0006380 A1 | 1/2004 | Buck et al. |
| 2004/0181239 A1 | 9/2004 | Dorn et al. |
| 2004/0215133 A1 | 10/2004 | Weber et al. |
| 2005/0004515 A1 | 1/2005 | Hart et al. |
| 2005/0060016 A1 | 3/2005 | Wu et al. |
| 2005/0080476 A1 | 4/2005 | Gunderson et al. |
| 2006/0173524 A1 | 8/2006 | Salahieh et al. |
| 2006/0282150 A1* | 12/2006 | Olson .................... A61F 2/966 623/1.11 |
| 2007/0060999 A1* | 3/2007 | Randall .................... A61F 2/95 623/1.11 |

FOREIGN PATENT DOCUMENTS

| | | |
|---|---|---|
| WO | 02/087470 | 11/2002 |
| WO | 2005/053574 | 6/2005 |

* cited by examiner

*Primary Examiner* — Katherine M Shi

(57) ABSTRACT

Device useful for implanting an implantable device within the vasculature of a patient. The device includes a deployment line, a control component for actuating the deployment line, and an actuation mechanism for translating constant-rate actuation of the control component into variable rate retraction of the deployment line from a remotely deployable implantable device. Suitable implantable devices include, for example, stents and stent grafts.

9 Claims, 6 Drawing Sheets

DEVICE FOR DEPLOYING AN IMPLANTABLE MEDICAL DEVICE

BACKGROUND OF THE INVENTION

1. Field of the Invention

The present invention relates to devices used to implant medical devices within a patient's vasculature.

2. Description of Related Art

It is known to deliver various implantable medical devices to a patient's vasculature. Typically, an implantable device is delivered to a treatment site (such as coronary artery, carotid artery, etc.) by locating the device near the distal end of a suitable catheter. The catheter can then be percutaneously introduced and guided to the deliver site where the device is then delivered.

Known implantable medical devices include, for example, stents and stent grafts (hereinafter collectively "stents"). Stents can be loaded on a balloon and delivered to the treatment site by inflating and then deflating the balloon. After balloon deflation the catheter can be withdrawn, leaving the stent implanted at the treatment site.

Another form of stents include the known "self-expanding" stents. Such stents are loaded onto the distal end of a catheter and delivered to the treatment site in a compressed state. Typically the stent is held in the compressed state by an outer sheath or tubular member. To deliver the stent the outer sheath, or tubular member, is, typically, withdrawn proximally along the catheter, thus allowing the stent to self-expand.

One means for withdrawing the sheath or tubular member is to provide the sheath or tubular member with a deployment line that extends proximally for the length of the catheter so that the physician can grasp the deployment line by hand. Upon locating the stent at the delivery site, the physician then slowly pulls back the deployment line, thereby gradually removing the sheath or tubular member and, thus, allowing the stent to self-expand.

A further means for withdrawing the sheath or tubular member includes providing the sheath or tubular member with a deployment line that extends proximally along the length of the catheter and into a suitable hand-held device. The deployment line can be retracted by operating a suitable mechanical device, such as that disclosed in US Patent Application Publication Number 2004/0006380 A1, in the names of Buck, et al. The device disclosed in the Buck et al. document includes a tubular member compressing the stent. The tubular member is capable of being retracted at a constant rate by rotating a knob at a constant rate. As the tubular member is retracted, the stent self-expands and is thus deployed.

One potential problem with the above-described delivery systems is that while retracting the outer sheath or tubular member at a relatively constant rate, it is common for the self-expanding stent to jump or slip out distally of the sheath or tubular member, thus causing poor stent placement or perhaps damage to the patient's vasculature.

Accordingly, it is a purpose of the present invention to overcome such shortcomings by providing a device that will allow for more accurate placement of implantable devices.

SUMMARY OF THE INVENTION

A device for retracting a deployment line of a remotely deployable implantable device comprising: a deployment line adapted to effect deployment of the remotely deployable implantable device; a control component for actuating the deployment line; an actuation mechanism for translating constant-rate actuation of the control component into variable rate retraction of the deployment line from the remotely deployable implantable device.

DESCRIPTION OF THE DRAWINGS

The operation of the present invention should become apparent from the following description when considered in conjunction with the accompanying drawings, in which.

DETAILED DESCRIPTION OF THE INVENTION

Figure 1:
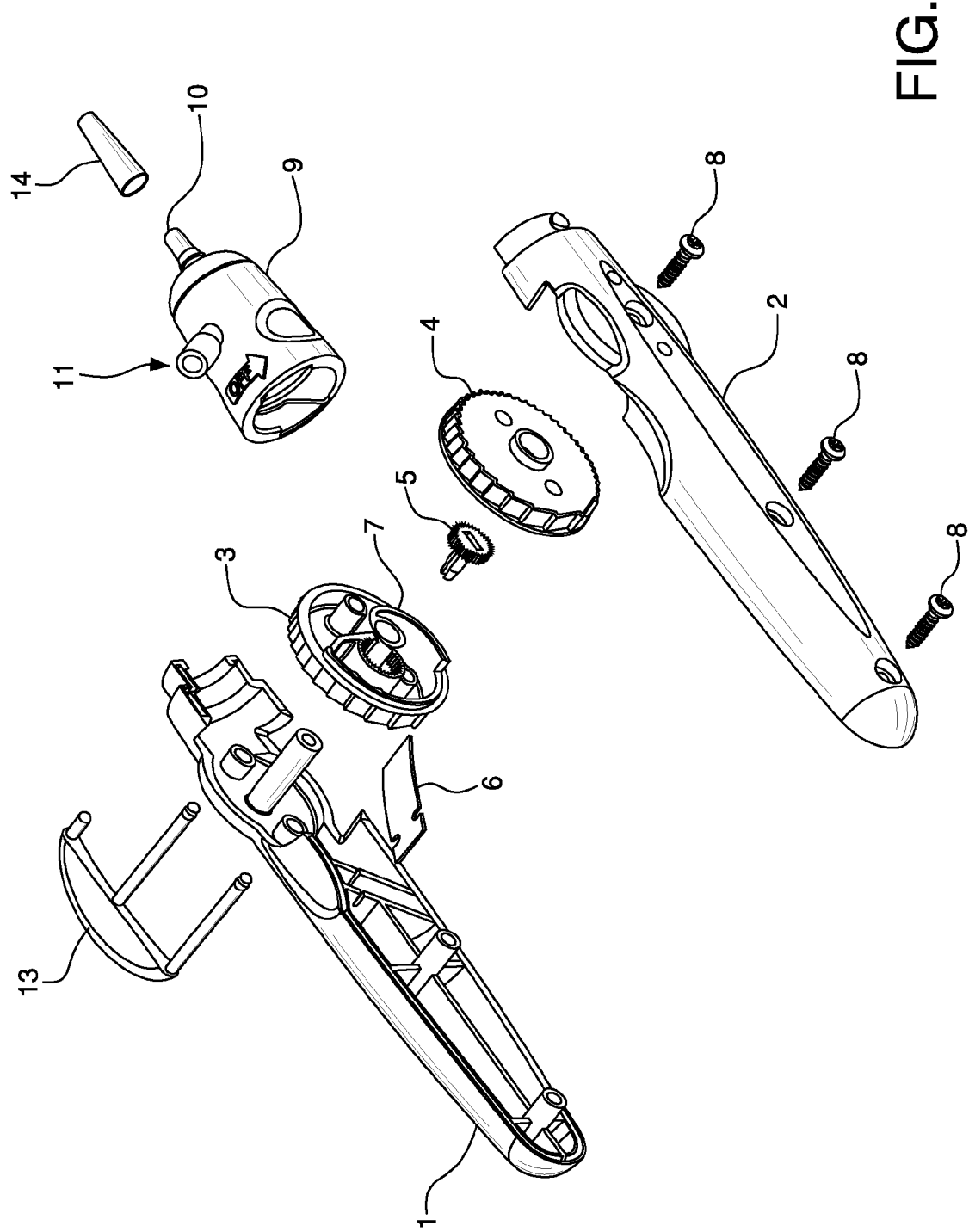
FIG. 1 is an exploded view of a device according to the present invention.

The present invention comprises a device for retracting a deployment line of a remotely deployable implantable device comprising: a deployment line adapted to effect deployment of the remotely deployable implantable device; a control component for actuating the deployment line; an actuation mechanism for translating constant-rate actuation of the control component into variable rate retraction of the deployment line from the remotely deployable implantable device.

The deployment line is preferably attached at its proximal end to the control component and/or actuation mechanism and attached at its distal end to a sheath or tubular member located at or near the distal end of a catheter shaft. Suitable deployment line materials include, for example, polymer materials, metals, etc. For example, the deployment line may be a polymer line or cord, a metal wire, or a braided cable. In an aspect of the invention metal wires could comprise stainless steel or Nitinol wire. In a further aspect of the invention the deployment line could comprise nylon cord or fiber. In a further aspect of the invention the line material comprises polytetrafluoroethylene. In a still further aspect of the invention the line material comprises expanded polytetrafluoroethylene, such as ePTFE fiber available from W. L. Gore & Associates, Inc. For example, suitable ePTFE fiber available from W. L. Gore & Associates, Inc. is available under Gore part number MD26274.

The control component can be any suitable component that is capable of being operated by hand. In an aspect of the invention the control component is a rotary control component for actuating the deployment line. In a further aspect of the invention the control component is a thumb operable wheel having a plurality of teeth extending from its outer surface. The teeth can be spaced apart in substantially equal distances from tooth-to-tooth. In an aspect of the invention the teeth can be spaced apart in variable distances. In an aspect of the invention the thumb operable wheel can be manufactured from acrylonitrile-butadiene-styrene ("ABS").

The actuation mechanism is capable of translating constant-rate actuation of the control component into variable rate retraction of the deployment line. In an aspect of the invention the actuation mechanism translates constant-rate actuation of the control component into an increased rate of retraction of the deployment line. In a further aspect of the invention the actuation mechanism comprises a cam device. In a still further aspect of the invention the actuation mechanism comprises a variable pitch lead screw. The skilled artisan will understand the various forms of suitable devices that are capable of translating constant-rate actuation of a control component into variable rate retration of the deployment line. The above-discussed cam device and variable pitch lead screw are illustrative, preferred actuation mechanisms, but should not be viewed as limiting.

The remotely deployable device is typically loaded onto the distal end of a catheter shaft (discussed below), and can be any device designed to be deployed within a patient's vasculature. Examples of remotely deployable devices include stents and stent grafts (collectively "stents"). Particularly attractive remotely deployable devices are self-expanding stents.

The distal end of the device can be designed to be joined with the proximal end of a suitable catheter shaft. A suitable strain relief member (e.g., a tubular member) can be provided between the device and catheter shaft to provide a transition from the relatively stiff device to the relatively flexible catheter shaft. A suitable elastomer material may be particularly suited for this purpose. The catheter shaft should have at least one lumen extending for at least a portion of the length of the catheter. This lumen should be sized to accept the deployment line therein. Moreover, the catheter shaft can be provided with a guidewire receiving lumen that extends for at least a portion of the length of the catheter shaft. The guidewire receiving lumen can be in fluid communication with at least two openings or ports. Preferably, one port is located at the distal end of the catheter shaft and a second port is located proximal thereto either at a point along the catheter shaft or at the proximal end of the catheter shaft near the distal end of the device.

In an aspect of the invention the distal end of the device is provided with an opening or port which allows the deployment line to extend from the device distally into the at least one lumen of the catheter. The deployment line can extend distally to near the distal end of the catheter. In an aspect of the invention a port can be provided in the catheter shaft at a point proximal to the remotely deployable device. The deployment line can exit through the port and can be attached to a suitable sheath or tubular member that holds the remotely deployable device in a compressed state.

In an aspect of the invention a self-expanding stent is loaded onto or otherwise located at or near the distal end of the catheter. The self-expanding stent is held in a compressed state by a sheath or tubular member. The sheath or tubular member is preferably at least as long as the stent. The sheath or tubular member is joined with or attached to the distal end of the deployment line. The deployment line preferably exits the catheter lumen through an opening in the catheter wall proximal to the sheath or tubular member.

The invention can best be further understood by referring to the figures wherein certain specific aspects of the invention are shown.

Turning to FIG. 1 there is shown in exploded view a device according to the present invention. As shown, the device includes left 1 and right 2 housing assemblies. The housing assemblies can comprise any suitable material. In an aspect of the invention the housing assemblies comprise ABS. Also shown are left 3 and right 4 wheels that can be snap-fit together in conjunction with pin 5 to form a control component according to the invention, in this case a thumb wheel. Pin 5 can be utilized to attach the proximal end of a deployment line (not shown) to the wheel and in contact with a suitable actuation mechanism, in this case cam device 7. Left and right wheels can comprise any suitable material, such as ABS. Stiff, yet resilient spring element 6 is provided to work in conjunction with the teeth located on the outer surfaces of left 3 and right 4 wheels. Spring element 6 will have some flexibility, but will be stiff enough to prevent the thumb wheel from rolling back in a clock-wise direction. Spring element 6 can comprise any suitable material and is locked into place by any suitable means. In an aspect of the invention, spring element 6 can comprise ABS or stainless steel. Locking mechanism 13 is provided to lock the wheel assembly into place for shipment of the device. Screws 8 are provided to secure together left 1 and right 2 housing assemblies once they are snapped together. Nose cone 9 can be snap-fit (or screwed) onto the distal end of the left 1 and right 2 housing assemblies once they are assembled. Nose cone 9 can comprise any suitable material, such as ABS. Nose cone 9 includes a distal opening 10 that can be in fluid communication with a lumen in a catheter which can be joined or attached to the distal end of the nose cone 9. Nose cone 9 can additionally include a proximal opening (not shown) that can be in fluid communication with distal opening 10. Strain relief element 14 can be attached to or joined with the distal end of nose cone 9. Strain relief element 14 is provided with at least one lumen extending from its proximal end to its distal end, the lumen being in fluid communication with distal opening 10. Finally, flushing port 11 can be provided to the nose cone 9 and can be in fluid communication with the distal opening 10, to allow for flushing of the catheter lumen. Typically, flushing port 11 will be provided with a suitable luer-type fitting to allow for the attaching of, for example, a syringe for flushing the catheter lumen with saline solution, etc. Moreover, a suitable means for preventing the flushing fluid from exiting the proximal opening can be provided at the proximal opening (e.g., a suitable gasket or resin material).

Figure 2:
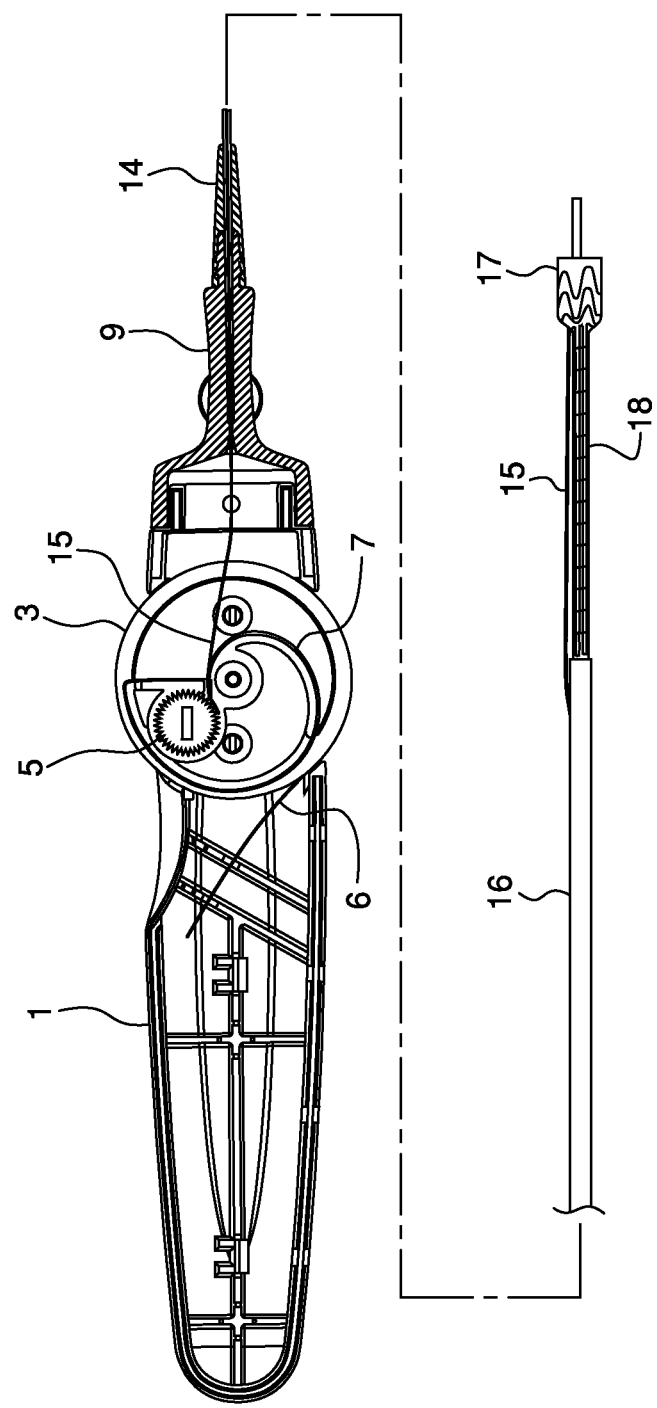
FIG. 2 is a perspective view of a device according to the present invention.

Turning to FIG. 2, there is shown in partial cross-section a fully assembled device according to the invention, attached to a catheter shaft 16. As seen, deployment line 15 is attached to left wheel 3 by first attaching the proximal end of deployment line 15 to pin 5 (such as by tying or wrapping the deployment line to the pin 5). Pin 5 can then be snap-fit into left wheel 3. Deployment line 15 is in contact with cam device 7 and extends distally through a lumen in nose cone 9. Nose cone 9 is provided with a lumen that extends from its proximal end to its distal end. Strain relief element 14 is attached to the distal end of nose cone 9 (such as by snap-fit, bonding, or other suitable means). Strain relief element 14 also includes a lumen that extends from the proximal end of the element to its distal end. The strain relief element lumen is in fluid communication with the lumen of nose cone 9. Catheter shaft 16 is also provided with a lumen. The catheter shaft lumen extends from the shaft proximal end to a point distal thereto. As shown, deployment line 15 extends distally through the lumen in catheter shaft 16 and exits the shaft through a port located near the distal end on the catheter shaft, but proximal to sheath 18 and stent 17. The catheter shaft may also be provided with a second lumen for accepting a suitable guide wire which can be used to help guide the catheter to a treatment site, as is well known in the art. Stent 17 and sheath 18 are shown mounted at the distal end of the catheter shaft 16, wherein the stent is shown in a partially deployed state.

Figure 3A:
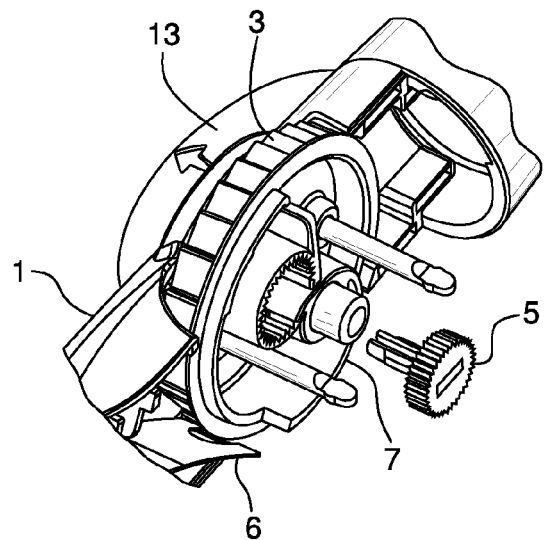
FIGS. 3A-3F show loading a deployment line onto a device according to the present invention.
Figure 3B:
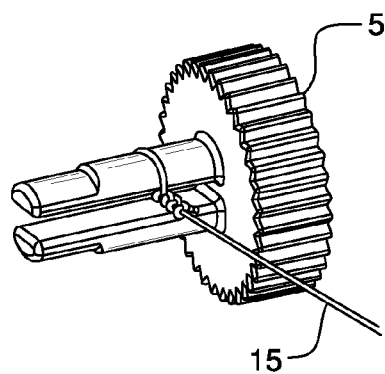
Figure 3C:
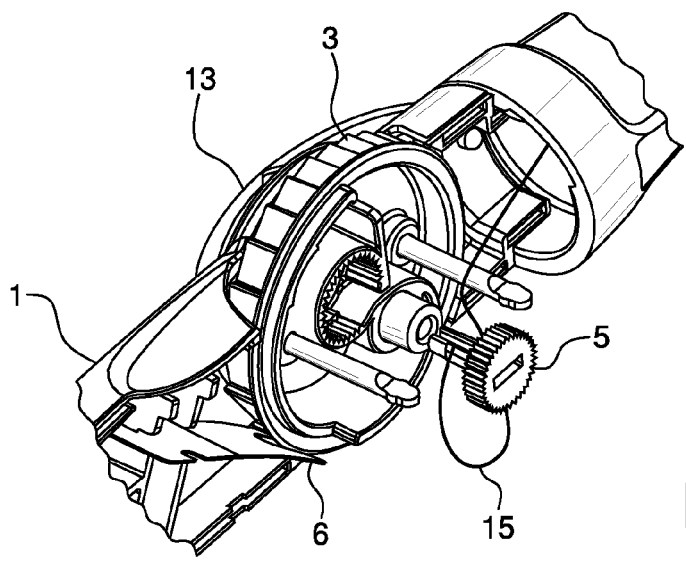
Figure 3D:
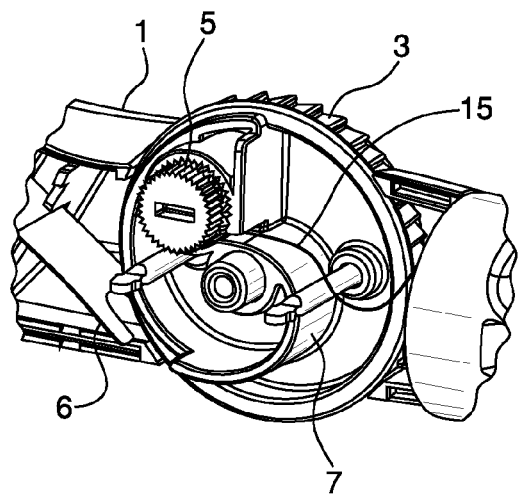
Figure 3E:
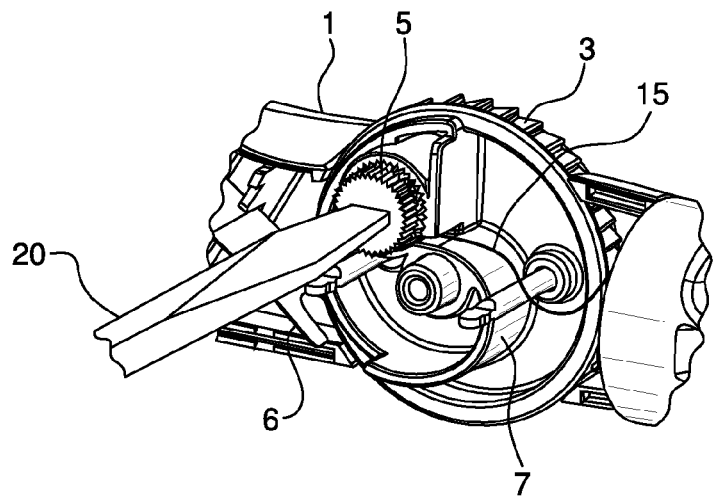
Figure 3F:
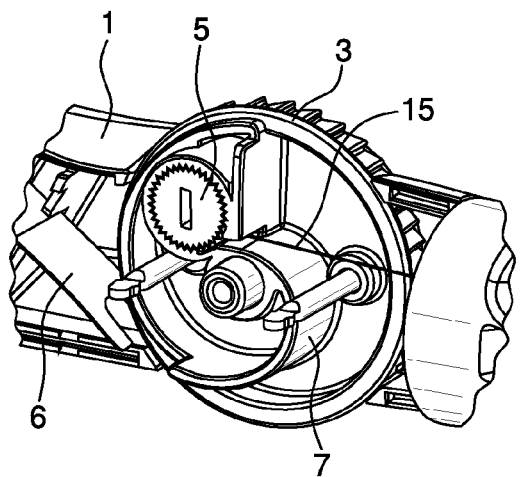

Turning to FIGS. 3A through 3F steps taken to attach deployment line 15 are illustrated. The device is shown in FIG. 3A prior to attaching deployment line 15 to pin 5. Prior to inserting pin 5 into the device, the proximal end of deployment line 15 is attached to (in this case tied to) pin 5, as shown in FIG. 3B. The distal end of the deployment line 15 can then be threaded through the distal end of the device and through the nose cone (not shown), lumen of the strain relief element (not shown), through the lumen of the catheter shaft (not shown), and attached to a sheath at the distal end of the catheter shaft. Pin 5 can then be aligned with a suitable bore in left housing assembly 1, as shown in FIG. 3C, while leaving slack in the deployment line 15. Pin 5 can then be partially inserted into the bore, while leaving slack in the deployment line, as shown in FIG. 3D. Screw driver 20 can then be used to push pin 5 into the bore and to rotate pin 5 counter-clockwise to take-up the slack in deployment line 15. As shown in FIG. 3F, deployment line 15 is sufficiently taught so that there is essentially no slack in deployment line 15. Right housing assembly 2 can then be snapped together with left housing assembly 1, completing assembly of the device.

Figure 4:
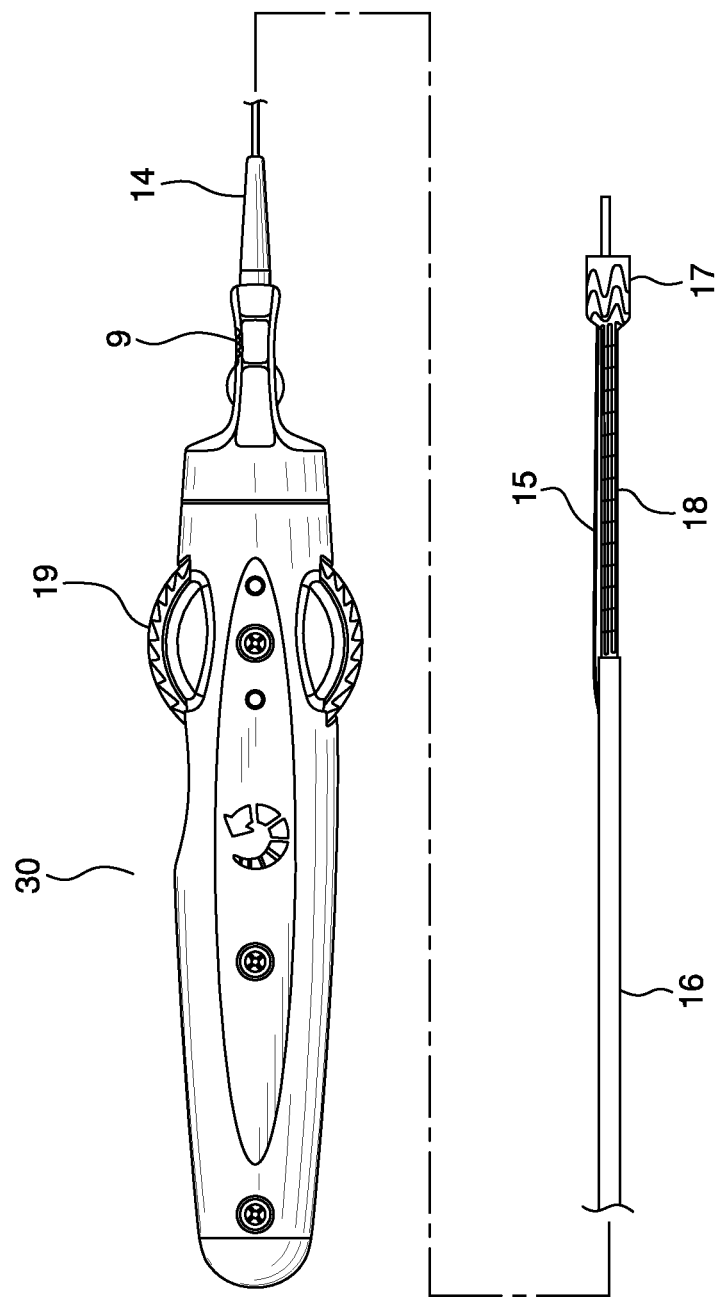
FIG. 4 is a side view of a device according to the present invention.

FIG. 4 shows the device 30 in final assembled form. As can be seen, left 3 and right 4 wheels are now snapped together forming a thumb wheel 19, having teeth on the outer surface thereof. Thumb wheel 19 can be easily rotated by the physician while grasping the device with one hand. As the thumb wheel 19 is rotated in a counter clock-wise direction an audible click sound will be provided by spring element 6, acting in conjunction with the teeth on wheel 19. Moreover, spring element 6 will also prevent the thumb wheel from slipping back in the clock-wise direction by locking with the teeth on the thumb wheel. Strain relief element 14 is shown attached to the distal end of nose cone 9. Catheter 16 is attached to the distal end of strain relief element 14. As can be seen, deployment line 15 extends distally through nose cone 9, through strain relief element 14, through catheter 16, out a port located in the catheter shaft wall, and is attached to sheath 18. Sheath 18 is shown partially removed from stent 17.

In an aspect of the invention, the teeth on the thumb wheel are not evenly spaced apart about the wheel. The teeth can be spaced at a variable distance apart such that rotation of the wheel will result in an audible clicking sound (caused by the teeth working in conjunction with the spring element) as the deployment line is retracted a predetermined interval. For example, the teeth could be spaced apart at variable distances such that an audible click will be heard for every 2 mm that the deployment line is retracted.

In a further aspect of the invention, nose cone 9 can be releasably attached to (e.g., snap fit, screwed on, etc.) the distal end of the housing assembly. This aspect provides the device with a "bail-out" feature in the event that rapid deployment of the remotely deployable device is desirable or necessary. For example, if rapid deployment of the remotely deployable device is desired, the physician could simply unsnap or twist the nose cone 9 from the housing assembly and rapidly pull the housing assembly in a proximal direction (thus resulting in the deployment line being rapidly withdrawn) to quickly deploy the remotely deployable device.

Figure 5:
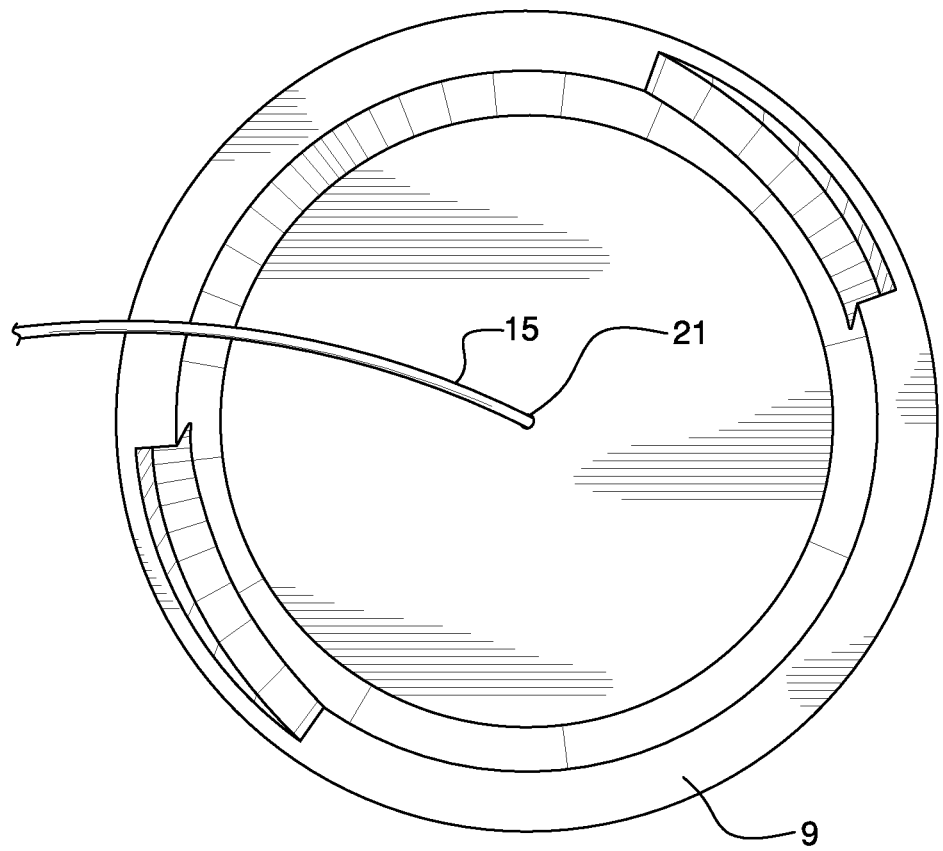
FIG. 5 shows the proximal side of a removable nose cone according to an aspect of the invention.

In a further aspect of the invention, the nose cone 9 can include a proximal opening 21, as shown in FIG. 5. A lumen can extend from the proximal end opening 21 to the distal end opening 10. Deployment line 15 can extend through proximal end opening 21, through the lumen and through distal end opening 10. When a flushing port is provided (as discussed above), the flushing port can be located distal to the proximal end opening 21 and proximal to the distal end opening 10. To prevent flushing fluid from entering the housing assembly, a suitable gasket material can be supplied to the proximal end opening 21. The gasket material should allow for the deployment line 15 to be withdrawn proximally, but should also prevent unwanted fluid from entering the housing assembly. A suitable gasket material in this regard can be a UV-curable adhesive or resin that will bond to the housing assembly (e.g., bond to an ABS material), but will not bond to the deployment line (e.g., PTFE or ePTFE). One such UV-curable adhesive is Loctite® UV-initiating cyanoacrylate.

In a still further aspect of the invention rather than the actuation mechanism translating constant-rate actuation of the control component into variable rate retraction of the deployment line, the actuation mechanism can provide constant rate retraction of the deployment line. For example, instead of a cam device as the actuation mechanism a cylinder could be used. The device could still include the wheel having a plurality of teeth used in conjunction with the spring element to obtain the audible clicking sound (discussed above) as the deployment line is retracted.

The device, catheter shaft, and remotely deployable member can be used as follows. The distal tip of the catheter can be advanced through a patient's vasculature (with or without assistance from a guide wire). Upon locating the stent 17 at the treatment site, wheel 19 can be carefully rotated in a counter-clockwise direction by the physician. Although wheel 19 is rotated at a relatively constant rate, deployment line 15 will be retracted proximally at an increasing rate due to the design of the surface of cam device 7. As will be appreciated, the more the thumb wheel 19 is rotated, the faster the retraction rate of deployment line 15 will be. Thus, as the stent is expanded (due to the retraction of sheath 18) it will first begin to expand relatively slowly and the expansion rate will increase as the thumb wheel is turned. Such a "slow-to-quick" expansion of the stent will help to prevent the stent from jumping, thus resulting in more accurate placement of the stent, as compared to the state of the art systems. Once the stent has been fully expanded and placed, the catheter can be proximally withdrawn from the patient.

While particular embodiments of the present invention have been illustrated and described herein, the present invention should not be limited to such illustrations and descriptions. It should be apparent that changes and modifications may be incorporated and embodied as part of the present invention within the scope of the following claims.

What is claimed:

1. A device for retracting a deployment line of a remotely deployable implantable device comprising:
    a deployment line adapted to effect deployment of the remotely deployable implantable device and having a proximal end and a distal end;
    a control component for actuating the deployment line;
    an actuation mechanism for translating constant-rate actuation of the control component into variable rate retraction of the deployment line from the remotely deployable implantable device; and
    a housing component having a proximal end and a distal end;
    wherein said control component comprises a bore and a pin element inserted into said bore and in contact with and attached to the proximal end of said deployment line.

2. The device of claim 1, wherein the actuation mechanism comprises a cam.

3. The device of claim 1, wherein the actuation mechanism comprises a variable pitch lead screw.

4. The device of claim 1, wherein the remotely deployable implantable device comprises a self-expanding device.

5. The device of claim 1, wherein the remotely deployable implantable device comprises a stent.

6. The device of claim 1, wherein the remotely deployable implantable device comprises an implantable filter.

7. The device of claim 1, wherein the control component is a rotary control component configured to rotate about an axis of rotation, and wherein the bore and the pin element are spaced apart from the axis of rotation such that the proximal end of the deployment line is connected to the control component outside the axis of rotation.

8. The device of claim 1, wherein the pin element is configured to facilitate rotation of the pin within the bore to take up slack in the deployment line during assembly of the device without movement of the actuation mechanism.

9. The device of claim 8, wherein the pin element is configured to facilitate the rotation of the pin while partially inserted within the bore, wherein the pin element includes a head with an irregular surface about a perimeter of the head, and wherein the bore of the control component includes a mating irregular surface to prevent, once the pin is fully inserted within the bore during assembly of the device, the pin from rotating within the bore.

\* \* \* \* \*